United States Patent [19]

Minagawa et al.

[11] 4,255,301
[45] Mar. 10, 1981

[54] GLYCOL CARBONATE ESTER STABILIZERS FOR SYNTHETIC RESINS

[75] Inventors: Motonobu Minagawa, Koshigaya; Yutaka Nakahara, Iwatsuiki; Naohiro Kubota, Urawa, all of Japan

[73] Assignee: Argus Chemical Corporation, Brooklyn, N.Y.

[21] Appl. No.: 904,524

[22] Filed: May 10, 1978

[30] Foreign Application Priority Data

May 10, 1977 [JP] Japan ................................. 52-53586

[51] Int. Cl.³ ............................................... C08K 5/04
[52] U.S. Cl. ............................ 260/18 TN; 252/399; 252/404; 252/406; 260/22 A; 260/23 XA; 260/23 H; 260/45.7 PH; 260/45.95 R; 260/45.95 D; 260/45.85 R; 260/45.75 N; 260/45.8 N; 260/340.7; 260/347.4; 260/463; 528/196
[58] Field of Search ......... 260/23 XA, 23 H, 23.7 M, 260/22 A, 22 CQ, 45.95 D, 45.85 A, 45.85 R, 45.8 N, 45.85 S, 45.95 R, 45.75 N, 45.7 PH, 18 TN, 463, 47 XA, 340.7, 347.4; 252/406, 399, 404

[56] References Cited

U.S. PATENT DOCUMENTS

| | | |
|---|---|---|
| 2,945,008 | 7/1960 | Caldwell et al. ............... 260/47 XA |
| 2,964,797 | 12/1960 | Peilstocker et al. ............. 260/47 XA |
| 3,359,242 | 12/1967 | Seeliger ................... 260/463 |
| 3,360,501 | 12/1967 | Widmer et al. ..................... 260/463 |
| 3,449,298 | 6/1969 | Matzner ................... 260/463 |
| 3,475,372 | 10/1969 | Gable ........................... 260/47 XA |
| 3,489,716 | 1/1970 | Calkins ......................... 260/47 XA |
| 3,546,332 | 12/1970 | Merriam et al. ................. 260/47 XA |
| 3,549,682 | 12/1970 | Vernaleken et al. ............ 260/47 XA |
| 3,631,200 | 12/1971 | Nehring et al. ..................... 260/463 |

Primary Examiner—V. P. Hoke
Attorney, Agent, or Firm—Otto S. Kauder

[57] ABSTRACT

Stabilizer compositions comprising a polymer stabilizer and a carbonate ester of cyclic dihydroxy compounds protect synthetic resins against the harmful effects of light having a wavelength less than 400 nanometers. The carbonate ester can be represented by the formula

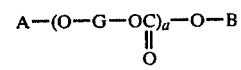

in which a is a number from 1 to 50, A is hydrogen or

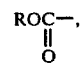

B is R' or —G—OH, R and R' are independently alkyl, alkoxyalkyl, cycloalkyl, aryl, aryloxyalkyl, aralkyl, or alkaryl groups, and G in at least one occurrence is a residue of a cycloaliphatic or non-aromatic oxygen heterocyclic dihydroxy compound having 3 to 20 carbon atoms and 1 or 2 rings of 3 to 12 members, of which up to 4 can be oxygen. Additional occurrences of G can be aliphatic glycol or bisphenol residues if desired. The polymer stabilizer included in the stabilizer compositions with carbonate esters of cyclic dihydroxy compounds can include metal carboxylate salts 1,2-epoxides, phenols, organic phosphites, esters of thiodipropionic acid, 2-hydroxybenzophenones, 2(2'-hydroxyaryl)-benzotriazoles, nickel phenolates, and carboxylic acids of 2,2,6,6-tetraalkylpiperidine-4-alcohols.

There are also provided stabilized synthetic resin compositions comprising a stabilizer composition including a carbonate ester of a cyclic dihydroxy compound as defined.

24 Claims, No Drawings

GLYCOL CARBONATE ESTER STABILIZERS FOR SYNTHETIC RESINS

BACKGROUND OF THE INVENTION

This invention relates to polymer stabilizer compositions comprising carbonate esters of cycloaliphatic dihydric alcohols and to certain novel carbonate esters of alkylidenebis dicyclohexanol compounds useful in stabilizer compositions for synthetic resins subject to deterioration on heating at 150° C. or higher or on exposure to light of wave length shorter than 400 nanometers.

As a class, organic carbonate esters are well known, see for example the review by W. Tuemmler in Kirk-Othmer Encyclopedia of Chemical Technology, Second Edition, (J. Wiley-Interscience, New York 1964), vol. 4, pages 386 to 393. Organic dihydroxy compounds give either cyclic or polymeric carbonate esters depending on the number of carbon atoms between hydroxyl groups, and the pioneering studies on polymerization and ring formation by W. H. Carothers and co-workers included work with dihydric alcohol carbonates having molecular weights up to about 5000 (see J. Amer. Chem. Soc. 1930 Vol. 52 pages 314–326).

Carbonate esters of dihydric phenols are also well known. With molecular weights in the range of 10,000 to 100,000, preferably 18,000 and higher, carbonate esters of bisphenols having two benzenoid rings connected through a linking group such as alkylidene, cycloalkylidene, or sulfonyl constitute tough clear plastics useful in the forms of films, fibers, and molded articles. Much of the very extensive patent literature on thermoplastic carbonate polyesters has been summarized by L. Bottonbruch in "Encyclopedia of Polymer Science and Technology" (N. Bikales, ed., J. Wiley Interscience, New York 1969, vol. 10 pages 710–764).

There are only a few scattered mentions of carbonate esters of cycloaliphatic dihydric alcohols, M. Gawlak et al in "Chemistry and Industry" 1962, vol. 25, page 1148 have described the bis(ethyl carbonate) esters of the cis and trans/isomers of 2,2,4,4-tetramethylcyclobutane-1,3-diol and their conversion to high melting carbonate esters along with carbon dioxide and 2,2,4-trimethyl-3-pentenal. G. A. Adam et al in "European Polymer Journal," 1976, vol. 12, pages 295–298 have described carbonate esters of a mixture of 4,4'-isopropylidenediphenol and cyclohexane-1,4-dimethanol containing 1 to 52.9 mole percent of the cyclohexane dimethanol and having lower crystallinities and glass transition temperatures than the diphenol homopolymer.

Certain carbonate esters of polyhydric phenols having molecular weights well below the range useful for mechanical strength, i.e. not more than 10,000, have been disclosed as stabilizers for olefin polymers and other kinds of organic material subject to deterioration on heating.

D. Bown et al. in U.S. Pat. Nos. 3,510,507 of May 5, 1970 and 3,691,132 of Sept. 12, 1972 disclosed polyolefins stabilized with polyphosphites, polyphosphates, polyphosphonites, polyphosphonates, polyborates, polycarbonates, and polysilanes which are condensation products of a 4,4'-bisphenol with a condensing or linking agent which may be of the ester type, such as the esters of triaryl or mixed aryl-alkyl compounds, or the acid halide type. Bown's condensation product stabilizers have molecular weights between 600 and 8000 or higher and are described by the structural formula,

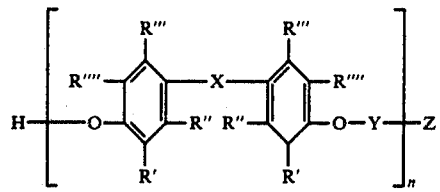

where X is selected from the group consisting of

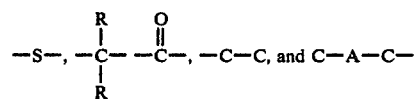

where A is a $C_1$ to $C_{16}$ alkylene or an arylene; R', R'', R''', and R'''' are selected from the group consisting of hydrogen, $C_1$ to $C_{18}$ alkyls, and an aryl group; Y is selected from the group of

where R is hydrogen, a $C_1$ to $C_{18}$ alkyl, or aryl;

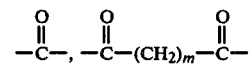

where m is 0 to 10, preferably 4 to 8,

where A' is $(CH_2)_n-S-(CH_2)_n$ or $-(CH_2)_n-S-(CH_2)_m-S-(CH_2)_n$ where n is 0 to 10, preferably 2 and m is 0 to 10, preferably 5;

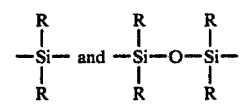

where R is an alkyl, preferably methyl, and Z is

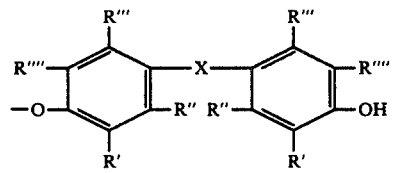

where R', R'', R''', R'''', and X correspond respectively to the R',R'',R''',R'''', and X previously selected when n has a value from 1 to 15, or Z may be derived from the compound used to introduce Y into the product when n has a value from 2 to 15, for example —R or —OR where R is hydrogen, an alkyl, or aryl. When Y in the formula of Bown's stabilizer is

the stabilizer is a type of hydroxyaryl phosphite. Similarly, when Y in the formula is

the stabilizer is a hydroxyaryl carbonate.

Bown's condensation products are described as especially effective in high molecular weight solid polyolefins when used together with a dialkyl sulfide costabilizer such as dilauryl thiodipropionate, distearyl thiodipropionate, ditridecyl thiodipropionate, dicetyl sulfide, bis(tetradecylmercapto) paraxylylene, and 10,24-dithiotetracontane.

J. Floyd et al in U.S. Pat. No. 4,032,510 of June 28, 1977 disclosed low molecular weight polycarbonate esters of bisphenols such as 2,2-bis(3-t-butyl-4-hydroxyphenylpropane) and 4,4'-butylidene bis(6-t-butyl-3-methylphenol) prepared in such a way as to contain few or no free phenolic hydroxyl groups as being highly effective heat and light stabilizers for polyolefins and giving a synergistic effect with distearyl thiodipropionate, tris (nonylphenyl) phosphite, and distearyl pentaerythritoldiphosphite.

SUMMARY OF THE INVENTION

In accordance with this invention, new synthetic resin stabilizer compositions comprising a known polymer stabilizer and a cyclic dihydric alcohol carbonate ester, in which the cyclic dihydric alcohol has one or two ring structures having three to twelve ring member atoms and up to 20 carbon atoms, are prepared. The carbonate ester components are oligomers with a degree of polymerization not in excess of 50 and have molecular weights ranging up to a maximum of about 15000, preferably from 300 to 7000 expressed as number average molecular weights determined, for example, by freezing point, boiling point, or vapor pressure change measurements, for highest effectiveness as ingredients of stabilized compositions for synthetic resins. The carbonate esters of the invention can contain a single non-aromatic cyclic dihydric alcohol residue or a plurality of cyclic dihydric alcohol residues, as well as residues of additional dihydroxy compounds which can be aliphatic dihydroxy compounds having 2 to 20 carbon atoms or bisphenols having 12 to 31 carbon atoms. The carbonate esters can be represented by the formula

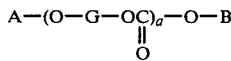

in which a is a number from 1 to 50, A is hydrogen or a group

B is a group R' or a dihydroxy compound residue —G—OH, R and R' independently of one another are alkyl, alkoxyalkyl, cycloalkyl, aryl, aryloxyalkyl, aralkyl, or alkaryl groups having 1 to 20 carbon atoms, and G independently at each occurrence is a residue of a dihydroxy compound selected from the group consisting of aliphatic dihydroxy compounds having 2 to 20 carbon atoms, bisphenols having 12 to 31 carbon atoms, and cyclic non-aromatic dihydroxy compounds having 3 to 20 carbon atoms and 0 to 4 ring oxygen atoms in 1 to 2 rings having 3 to 12 members, provided that at least one occurrence of G is a residue of a cyclic non-aromatic dihydroxy compound having 3 to 20 carbon atoms and 0 to 4 ring oxygen atoms in 1 to 2 rings of 3 to 12 members.

The new stabilizer compositions are especially effective in enhancing the resistance of synthetic resins, for example polyolefin, vinyl chloride polymer, polymethylene terephthalate, and acrylonitrile-butadiene-styrene polymers to deterioration on exposure to light of wave length shorter than 400 nanometers. The proportions of carbonate ester to known polymer stabilizer in such stabilizer compositions can range from 10 to 1 to about 1 to 50 by weight, and the amount of stabilizer composition used to stabilize a synthetic resin against the deleterious effects of light of wavelength shorter than 400 nanometers contributes 0.001 to 5 parts by weight per 100 parts of synthetic resin of carbonate ester according to this invention.

DESCRIPTION OF PREFERRED EMBODIMENTS

The cyclic dihydric alcohol carbonate ester components of the stabilizer composition of this invention are crystalline powders or grindable glassy solids. Unlike the many known polyhydric phenol carbonate resins and plastics, the carbonate esters of the invention have by themselves no useful mechanical strength, which is probably a result of the entirely different molecular weight range of the coesters of this invention as contrasted to known polyhydric phenol carbonate esters and polyhydric alcohol-polyhydric phenol carbonate coesters whose molecular weight for useful mechanical strength in fibers, films and molded articles, ranges from a 10000 minimum to above 100000.

When A and B in the formula

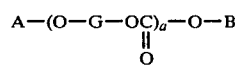

are groups of the type

and R' respectively, the R and R' alkyl, alkoxyalkyl, aryloxyalkyl, aralkyl, cycloalkyl, aryl or aryl or alkylaryl radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, phenyl, xylyl, tolyl, ethylphenyl, naphthyl, benzyl, 2-methylcyclohexyl, 6-dihydrocyclopentadienyl, dimethylbenzyl, p-dodecylbenzyl, 2-butoxyethyl, 2-methoxyethyl, 2-butoxypropyl, 2-phenoxyethyl, and 2(p-t-butylphenoxy) ethyl.

The cyclic non-aromatic dihydroxy compound which provides at least one G residue in the formula

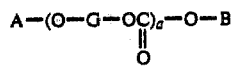

of the glycol carbonate ester of this invention can be a cycloaliphatic dihydroxy compound and an oxygen heterocyclic dihydric alcohol.

Useful cycloaliphatic dihydroxy compounds include 1-hydroxymethyl-1-hydroxy cyclopropane, 1,1-dihydroxymethylcyclobutane, 1-hydroxymethyl-1-hydroxy cyclobutane, 1,3-dihydroxy-2,2,4,4-tetramethylcyclobutane, 1,3-dihydroxy-2,4-diethylcyclobutane, 2,6-dihydroxymethyl-spiro-(3,3)-heptane, 1,2-dihydroxycyclopentane, 1,3-dihydroxycyclopentane, 1,2-dihydroxymethylcyclopentane, 1-hydroxy-2-hydroxymethylcyclopentane, 1,2-dihydroxycyclopentene-3, 1,6-dihydroxy-spiro-(4,4)-nonane, 1,2-bis(1-hydroxyethylcyclopentyl)ethane, 1,2-dihydroxycyclohexane, 1,3-dihydroxycyclohexane, 1,4-dihydroxycyclohexane, 1,2-dihydroxy-3-methylcyclohexan, 1,2-dihydroxy-4-methylcyclohexane, 1,3-dihydroxy-2,5,5-trimethylcyclohexane, 1,3-dihydroxy-2,2,5,5-tetramethylcyclohexane, 1,2-dihydroxymethylcyclohexane, 1,3-dihydroxymethylcyclohexane, 1,4-dihydroxymethylcyclohexane, 2,3-dihydroxybicyclo(4,4,0) decane, 1,8-dihydroxy-bicyclo (4,4,0) decane, 1,2-bis(4-hydroxycyclohexyl)propane, 1,2-dihydroxycycloheptane, 1,2-dihydroxycyclooctane, 1,3-di-hydroxycyclooctane, 1,4-dihydroxycyclooctane, 1,5-dihydroxycyclooctane, 1,2-dihydroxycyclononane, 1,5-dihydroxycyclononane, 1,2-dihydroxycyclodecane, 1,6-dihydroxycyclodecane, 1,2-dihydroxycyclododecane, and 1,4-dihydroxymethyl-bicyclo (2,2,1) heptane.

Particularly preferred among the cycloaliphatic dihydroxy compounds is 4,4'-isopropylidenedicyclohexanol. Useful oxygen heterocyclic dihydroxy compounds include 2,5-dihydroxytetrahydrofuran, 2,5-bis(hydroxymethyl)tetrahydrofuran, 2,5-bis(hydroxymethyl) 1,4-dioxane, 3,5-bis(hydroxymethyl)tetrahydropyran, isosorbide, 3,9-bis(2'-hydroxyethyl)-2,4,8,10-tetraoxaspiro(5,5) undecane, and 3,9-bis(2'-hydroxy-1',1'-dimethylethyl)-2,4,8,10-tetraoxa-spiro(5,5) undecane.

In addition to the cyclic non-aromatic dihydroxy compound residue G in the formula of the glycol carbonate ester of this invention there can also be residues G of aliphatic dihydric alcohols having 2 to 20 carbon atoms and residues G of bisphenols having 12 to 31 carbon atoms.

Representative g residues of dihydric alcohols include polymethlene radicals having 2 to 20 carbon atoms such as ethylene, 1,3-propylene, 1,4-butylene, 1,5-pentamethylene, 1,6-hexamethylene, and 1,12-dodecamethylene; alkylene radicals such as 1,2-propylene, 1,3-butylene, 2-ethylhexylene-1,3-and 9-octadecene-1,12-diyl; and alkylsubstituted alkylene radicals such as 2-methyl-2-ethyl-1, 3-propylene and 2-methyl-2-butyl-1, 3-propylene.

Representative G residues of bisphenols include residues of dihydric phenols having two benzenoid rings linked directly or through an ether, sulfide, sulfoxide, sulfone, cycloalkylidene, alkylidene, or arylalkylidene linking group. The benzenoid rings can be unsubstituted or substituted with alkyl, cycloalkyl, aryl, aralkyl, or alkaryl groups having up to 10 carbon atoms, of which preferably at least one is positioned ortho to a phenolic hydroxyl group. Useful bisphenols include 4,4'-sulfonyldiphenol, 3,3'-oxydiphenol, 4,4'-isopropylidenediphenol, 4,4'-cyclohexylidenebisphenol, and 1,2-bis(4'-hydroxyphenoxy)ethane. A preferred kind of G residue is a residue of an ortho-substituted bisphenol having two ortho-substituted phenolic groups linked directly or through a two valent hydrocarbon group, such as 2,2'-methylene bis(4-methyl-6-t-butyl-phenol), 2,2'-methylene bis(4-ethyl-6-t-butylphenol), 2,2'-methylene bis(4-methyl-6-(1-methylcyclohexyl) phenol), 2,2'-n-butylidene bis(b 4,6-dimethylphenol), bis-1,1-(2'-hydroxy-3'5'-dimethylphenyl)-3,5,5,-trimethylhexane, 2,2'-cyclohexylidene bis(4-ethyl-6-t-butylphenol), 4,4'-methylene bis(2-methyl-6-t-butylphenol), 4,4'-methylene bis(2,6-di-t-butylphenol), 4,4'-isopropylidene bis(2-phenylethylphenol), 4,4'-n-butylidene bis(3-methyl-6-t-butylphenol), 4,4'-cyclohexylidene bis(2-t-butylphenol), 4,4'-cyclohexylidene bis(2-cyclohexylphenol), and 4,4'-benzylidene bis(2-t-butyl-5-methylphenol), or of ortho-substituted bisphenols having two ortho-substituted phenolic groups linked through oxygen or sulfur, such as 4,4'-oxobis (3-methyl-6-isopropylphenol), 4,4'-thiobis(2-methyl-6-t-butylphenol), 4,4'-thiobis(3-methyl-6-t-butylphenol), 4,4'-sulfobis(3-methyl-6-t-butylphenol), bis(2-methyl-4-hydroxy-5-t-butylbenzyl) sulfide, bis(3,5-di-t-butyl-4-hydroxy benzyl) sulfide, 2,2'-thiobis (4-t-butyl-6-methylphenol), 2,2'-thiobis(4-methyl-6-t-butylphenol), and 2,2'-thiobis(4,6-di-t-butylphenol).

The cyclic dihydric alcohol carbonate esters of this invention can be prepared by the reaction of at least one cyclic dihydric alcohol HO—G—OH and any additional dihydroxy compound HO—G—OH with a carbonylating agent such as phosgene, a chloroformate ester, or a carbonate ester

in which R and R' are as previously defined, in one or several reaction stages. Acid acceptors such as ammonia, pyridine, organic amines, and inorganic alkalies can be used with phosgene and chloroformate esters, and acidic or alkaline transesterification catalysts can facilitate the reaction of

carbonate esters.

The molecular weight of the resulting ester is regulated by the proportions of carbonylating agent to HO—G—OH dihydroxy compound. The more closely the proportions of the carbonylating agent to dihydroxy compound HO—G—OH approach one to one compound equivalent to each reactant the higher the molecular weight of the resulting product.

Conversely, either reactant can be used in large excess to prepare products having nearly the lowest molecular weight possible, that is an ester having a in the formula

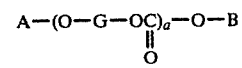

equal to one. Thus the product of the reaction between two moles of a cyclic dihydric alcohol and one mole of carbonylating agent is a relatively low molecular weight mixture of carbonate esters in which the bis(hydroxycycloalkyl carbonate)

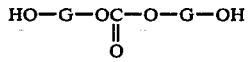

of the cyclic dihydric alcohol predominates, and the product of the reaction between two moles of a carbonate ester carbonylating agent

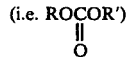

and one mole of cyclic dihydric alcohol is a relatively low molecular weight mixture of carbonate esters in which the dihydric alcohol bis-carbonate ester

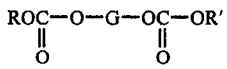

predominates.

Each of these products can then be used to prepare a higher molecular weight ester or coester of this invention by reaction with an appropriate compound. Thus the above bis(hydroxy cycloalkyl) carbonate ester can be caused to condense with an acid chloride or phenyl ester carbonylating agent with elimination of hydrogen chloride or phenol as side product respectively, to give a carbonate ester with a molecular weight depending on the relative proportions of reactants. Similarly, cyclic dihydric alcohol phenyl carbonate ester can be transesterified with a dihydroxy compound to displace phenol and give a carbonate ester of the dihydroxy compound present in each of the starting materials, which means that a coester can be made up of different dihydroxy compounds if each of the starting materials contains a different dihydroxy compound. Both techniques just described are essentially two stage reaction techniques that yield coesters of a relatively ordered structure in which the dihydroxy compound groups -G- are alternatingly linked through carbonate ester groups. Coesters prepared at elevated temperature, such as by the phenol ester transesterification technique, have the ordered alternating structure modified to a minor extent as a result of ester-ester interchange randomization.

Both the carbonate ester exchange reaction and the phosgene or chloroformate ester reaction can be facilitated by the use of catalysts. The carbonate ester reaction is suitably catalyzed by substances of sufficient alkalinity to convert phenol at least in part to the phenoxide ion, such as alkali and alkaline earth metals and their oxides, hydroxides, sulfide, cyanides, phenolates, hydrides, alcoholates, and carboxylates as well as aliphatic and cycloaliphatic amines, preferably tertiary amines to avoid the possible complication of amide formation. Suitable catalysts for the phosgene and chloroformate reactions include tertiary phosphines, and the hydrogen halide and alkyl halide addition salts thereof. Catalyst concentrations usefully range from 0.01% to about 5% by weight of reaction mixture. Preferred catalysts for the phosgene and chloroformate reactions have the ability to partition between water and immiscible hydrocarbon phase with a partition coefficient between 0.01 and 100.

Both the ester exchange reaction method of preparing the glycol carbonate ester of this invention and the phosgene and chloroformate methods can be carried out over a convenient range of reaction temperatures. The ester exchange reaction is conveniently carried out at elevated temperatures of the order of 80° to 210° C. with removal of the side product phenol or alcohol by distillation, suitably under diminished pressure. It is frequently helpful to begin the reaction by an atmospheric pressure cook, suitably with nitrogen or other inert gas protection over the reaction mass to preserve its light color, and apply vacuum gradually after a quantity of side product has accumulated for removal.

The phosgene or chloroformate reaction is conveniently carried out at ambient temperatures or as cold as −15° C. Elevated temperatures in the 40°–90° C. range can also be used.

Synthetic resins that can be stabilized with compositions comprising a cyclic dihydric alcohol carbonate ester according to this invention include alphaolefin polymers such as polyethylene, polypropylene, polybutene, poly-4-methylpentene, or copolymers thereof such as ethylene-vinylacetate copolymer, ethylenepropylene copolymer, polystyrene, polyvinylacetate, acrylic ester resins, copolymers from styrene and another monomer (for example, maleic anhydride, butadiene, acrylonitrile and so on), acrylonitrile-butadiene-styrene copolymer, acrylic acid ester-butadiene-styrene copolymer, methacrylic acid ester-butadiene-styrene copolymer, methacrylate ester resin such as polymethylmethacrylate, polyvinylalcohol, ethylene and butylene terephthalate polyesters, polyamide, polycarbonate, polyacetal, polyurethane, cellulosic resin, or phenolic resin, urea resin, melamine resin, epoxy resin, unsaturated polyester, silicone resin, halogen-containing resins such as polyvinyl chloride, polyvinylidene chloride, polyvinylidene fluoride and copolymers thereof, and further rubbers such as isoprene rubber, chloroprene rubber, and blends of the above resins.

Stabilizer compositions comprising a cyclic dihydric alcohol carbonate ester according to this invention can be formulated and marketed in liquid, solid, and paste forms. An inert solvent can be used to facilitate handling. The carbonate ester and known polymer stabilizers can also be solubilized in one another by heating, such as at 70°–160° C. for up to 4 hours, and then allowing the resulting melt to cool and harden sufficiently to be flaked and ground.

Known polymer stabilizers can be used in synthetic resin compositions together with the carbonate ester stabilizers of this invention and can be admixed with the latter. Such stabilizers include thiodipropionic acid esters, polyvalent metal salts of carboxylic acids, organic phosphites, 1,2-epoxides, polyhydric alcohols, polyhydric alcohol 3-alkylthiopropionic acid esters, ultraviolet stabilizers, and phenols. Representative thiodipropionic acid esters include di-n-dodecyl thiodipropionate, dihexadecyl thiodipropionate, distearyl thiodipropionate, n-octyl eicosanyl thiodipropionate and n-octadecyl cyclohexane-1,4-dimethanol thiodipropionate polyester. A comprehensive disclosure of useful thiodipropionate esters by M. Minagawa et al in U.S. Pat. No. 3,869,423, column 17 line 55 to column 19 line 54 is here incorporated by reference. When thiodipropionate esters are used the concentration based on 100 parts of polymer can range from 0.05 to about 0.75 parts by weight.

Representative polyvalent metal salts include zinc, calcium magnesium, barium, strontium and nickel salts of monocarboxylic acids having 6 to 24 carbon atoms, for example zinc benzoate, calcium palmitate, and nickel 2-ethylbutyrate. A comprehensive disclosure of useful metal salts by M. Minagawa et al in U.S. Pat. No. 3,869,423, column 19 line 56 column 20 line 35 is here incorporated by reference. When metal salts are used the concentration based on 100 parts by weight of polymer can range from 0.1 to about 3 parts by weight.

Representative organic phosphites include triisodecylphosphite, tris (nonylphenyl phosphite), and 4,4'-isopropylidene diphenol alkyl ($C_{12}$–$C_{15}$) phosphite. A comprehensive disclosure of useful organic phosphites by M. Minagawa in U.S. Pat. No. 3,849,370 column 13 line 63 to column 16 line 48 is here incorporated by reference. Typical use concentrations of organic phosphites are in the range from 0.02 part to about 2 parts by weight per 100 parts of polymer being stabilized.

Representative 1,2-epoxides that can be used in stabilizer compositions according to this invention include epoxysoybean oil, epoxylinseed oil, and 2-ethylhexyl epoxystearate. A comprehensive disclosure of 1,2-epoxides by M. Minagawa et al in U.S. Pat. No. 3,869,423 column 26 line 13 to line 39 is here incorporated by reference. Typical use concentrations of 1,2-epoxides range from 0.3 to about 6 parts by weight per 100 parts of synthetic resin composition.

Aliphatic polyhydroxy compounds can be included with stabilizer compositions of this invention in amounts corresponding to 0.1 to about 1 part per 100 parts of polymer being stabilized. Typical aliphatic polyhydroxy compounds are glycerol, polyglycerol, mono-, di-, and tri-pentaerythritol, mannitol, sorbitol, and partial esters of these with saturated and unsaturated fatty acids having 6 to 22 carbon atoms.

3-Alkylthio propionates of polyhydric alcohols can be included in stabilizer compositions of this invention in amounts corresponding to 0.02 to about 1 part per 100 parts of synthetic resin being stabilized. The propionate esters have 4 to about 34 carbon atoms in the alkylthiopropionate group, 2 to about 15 carbon atoms in the polyhydric alcohol group and 2 to about 8 ester groups in the molecule. Representative propionate esters are 2,2-dimethylpropanediol bis (3-n-dodecylthio-2-methylpropionate), pentaerythritol tetrakis(3-n-octylthiopropionate) and tris (3-n-octadecylthiopropionyloxyethyl) isocyanurate. For a further listing of useful 3-alkylthiopropionates the disclosure of A Onishi U.S. Pat. No. 3,629,194 can be consulted.

Ultraviolet stabilizers can be included in stabilizer compositions of this invention in amounts corresponding to 0.05 to about 1 part per 100 parts of synthetic resin being protected. Typical UV absorbing ultraviolet stablizers are 2-hydroxybenzophenones such as 2-hydroxy-4-n-octyloxybenzophenone and 2,4-dihydroxybenzophenone, and 2-(2'hydroxyphenyl)benzotriazoles such as 2-(hydroxy-5'-methylphenyl)benzotriazole and 2-(2'-hydroxy-5'-t-butylphenyl) 5,6-dichlorobenzotriazole and alkyl esters of alphacyano cinnamic acid and ring substituted alphacyanocinnamic acids. For a further listing of many useful ultraviolet absorbers the disclosure of U.S. Pat. No. 3,395,112 of July 30, 1968, particularly column 14 line 40 to column 19 line 33, as well as the review of G. R. Lappin in "Encyclopedia of Polymer Science and Technology", can be consulted.

Ultraviolet stabilizers that have little or no significant ultraviolet absorption and owe their effectiveness to a mode of action other than ultraviolet absorption can also be used. These stabilizers include nickel or cobalt salts and complexes such as butylamine-nickel thiobis(p-octylphenol-), nickel bis(N,N-dibutyldithiocarbamate), cobalt bis-(dicyclohexylphosphinodithioate), and alkyl hydroxyphenylalkylene phosphonic acid esters and ester salts of Mg, Ca, Sr, Ba, Ni, and Zn; aryl aromatic carboxylate esters such as bis(nonylphenyl)isophthalate, resorcinol bis(t-butyl-benzoate), and 2,4-di-t-butylphenyl 3,5-di-t-butyl-4-hydroxybenzoate; and particularly preferred, derivatives of 2,2,6,6-tetralkylpiperidines including those disclosed by K. Murayama in U.S. Pat. Nos. 3,840,494 and 3,899,464 and by B. Holt in U.S. Pat. No. 4,021,432. The preferred tetralkylpiperidines that can be used together with the cyclic dihydric alcohol carbonate esters according to this invention are carboxylic acid esters of an alcohol linked to the 4 position of a 2,2,6,6-tetramethylpiperidine having 15 to 75 carbon atoms and a piperidine nitrogen content ranging from 2 to 8 percent by weight, and can be represented by the formula

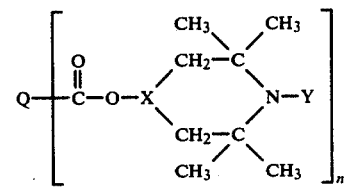

in which n is a whole number from 1 to 4, Y is selected from the group consisting of hydrogen and oxyl radical, X is a three valent linking member selected from the group consisting of —CH<,

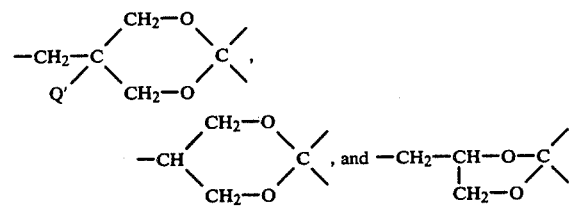

wherein Q' is a lower alkyl group, and Q is an organic group having a valence of n that can be open chain, carbocyclic, and heterocyclic.

Lower alkyl Q' groups include for example methyl, ethyl, propyl isopropyl, n-butyl, and isobutyl. Q groups can be for example alkyl such as ethyl, t-butyl, 2-heptyl, 1-undecyl, and 1-tricosanyl; aryl such as phenyl, t-butylphenyl, and 1-naphthyl; alkenyl such as allyl, methallyl, vinyl, propenyl, and 8-heptadecenyl; aralkyl such as benzyl and hydrocinnamyl; alkylene such as ethylene, 1,4-butylene, and decamethylene; alkenylene such as vinylene and 2-butene-1,4-diyl; cycloalkylene and cycloalkenylene such as methylcyclopentylene, cyclohexenylene, and bicycloheptenylene; and heterocyclic groups such as furyl, thienyl, and pyrrolidonyl.

Specific examples of such 2,2,6,6-tetramethylpiperidines include bis(2,2,6,-tetramethylpiperidin-4-yl) adipate, 2,2,6,6-tetramethylpiperidin-4-yl) 9,10-epoxystearate-1-oxyl radical, and tris(2,2,6,6-tetramethylpiperidine-4,4(1:3-dioxyisobutane-2-methyl))but-3-ene-1,2,3-tricarboxylate.

Phenols can be included in stabilizer compositions of this invention in amounts corresponding to 0.01 to about 0.5 part per 100 parts of synthetic resin being stabilized. Representative phenols include 2,6-di-t-butyl-p-cresol, 1,1,3-tris(2-methyl-4-hydroxy-5-t-butylphenyl)butane, and n-octadecyl 3,5-di-t-butyl-4-hydroxyphenylpropionate. A comprehensive disclosure of useful phenols by M. Minagawa et al in U.S. Pat. No. 3,849,370 column 16 line 49 to column 21 line 8 is here incorporated by reference.

The preparation of the stabilized resin composition is easily accomplished by conventional procedures. A heated two roll mill, for example, is a convenient compounding tool for blending stabilizer compositions of the invention with polyolefins, vinyl chloride polymers, ABS polymers, ethylenevinyl acetate copolymers and others.

The examples that follow illustrate the invention without limiting its scope. Synthesis Examples 1 and 2 describe the preparation of certain cyclic dihydric alcohol carbonate esters of this invention shown in Table 1 by techniques disclosed above. Examples 1-1 through 8-11 illustrate the use of carbonate ester stabilizers of this invention shown in Table 1 and identified by their Table 1 number, and stabilizer compositions comprising carbonate esters of this invention shown in Table 1, in the stabilization of olefin polymers, a vinyl chloride polymer, an ABS polymer, a butylene terephthalate polyester resin, and a polyurethane.

Formulas of the cyclic dihydric alcohol polycarbonate esters used in the subsequent examples are shown in Table-1.

TABLE 1

CYCLIC DIHYDRIC ALCOHOL CARBONATE ESTERS $A(-O-G-OC)_a-O-B$
$$\overset{\|}{O}$$

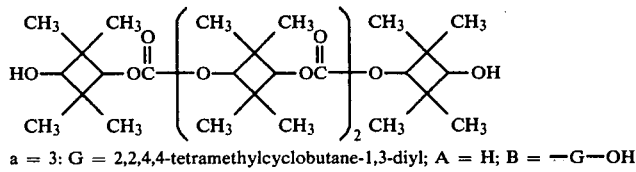

a = 3: G = 2,2,4,4-tetramethylcyclobutane-1,3-diyl; A = H; B = —G—OH

1

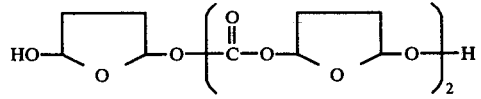

a = 2: G = tetrahydrofuran-2,5-diyl; A = H; B = —G—OH

2

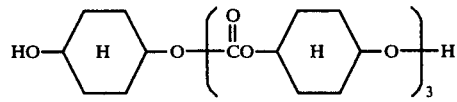

a = 3: G = cyclohexane-1,4-diyl; A = H; B = =G—OH

3

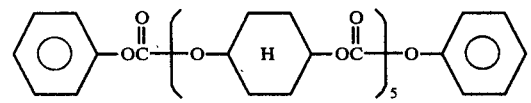

a = 5: G = cyclohexane-1,4-diyl; A = phenoxy carbonyl; B = phenyl

4

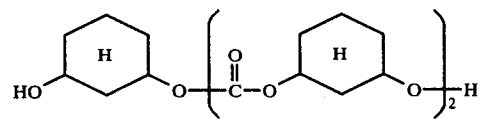

a = 2; G = cyclohexane-1,3-diyl; A = H; B = —G—OH

5

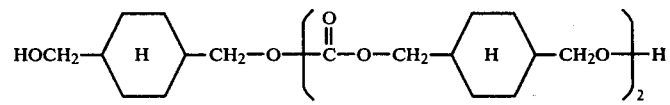

a = 2; G = cyclohexane-1,4-dimethylene; A = H; B = —G—OH

6

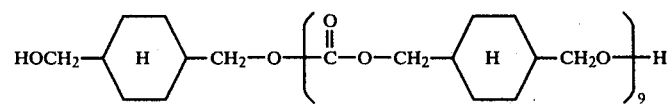

a = 9; G = cyclohexane-1,4-dimethylene; A = H; B = —G—OH

7

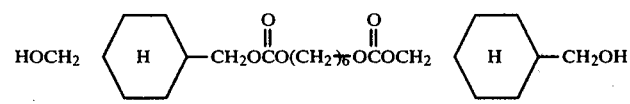

a = 2; G = cyclohexane-1,4-dimethylene and 1,6-hexamethylene; A = H; B = —G—OH

8

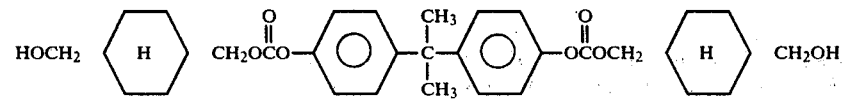

9

TABLE 1-continued
CYCLIC DIHYDRIC ALCOHOL CARBONATE ESTERS A(—O—G—OC)$_a$—O—B
$$\underset{O}{\overset{\parallel}{}}$$

a = 2; G = cyclohexane-1,4-dimethylene and 4,4'-isopropylidenediphenyl-
ene; A = H; B = G—OH

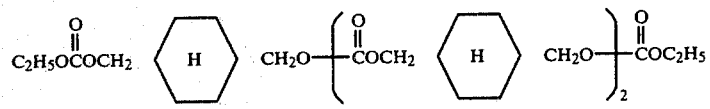

10 a = 3; G = cyclohexane-1,4-dimethylene; A = ethoxycarbonyl; B = ethyl

11 a = 3; G = cyclohexane-1,4-dimethylene and 2,2-dimethyl-1,3-
propylene; A = H; B = —G—OH

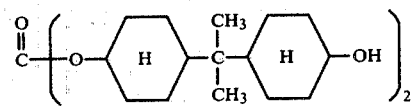

12

A = 1; G = 4,4'-isopropylidenedicyclohexylene; A = H; B = —G—OH

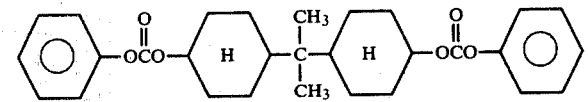

13 a = 1; G = 4,4'-isopropylidenedicyclohexylene; A = phenoxycarbonyl;
B = phenyl

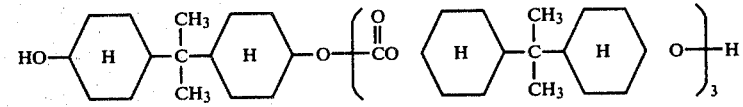

14 a = 3; G = 4,4 '-isopropylidenedicyclohexylene; A = H; B = —G—OH

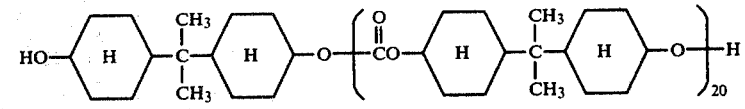

15 a = 20; G = 4,4'-isopropylidenedicyclohexylene; A = H; B = —G—OH

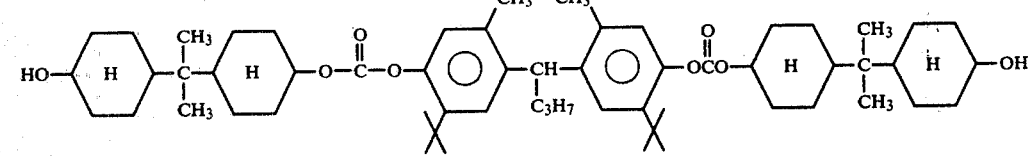

16 a = 2; G = 4,4'-isopropylidenedicyclohexylene and 4,4'-n-butyl-
idenebis-(2-t-butyl-5-methylphenylene); A = H; B = —G—OH

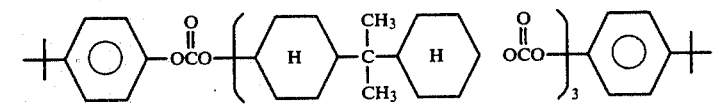

17 a = 3; G = 4,4'-isopropylidenedicyclohexylene; A = p-t-butylphenoxy-
carbonyl; B = p-t-butylphenyl

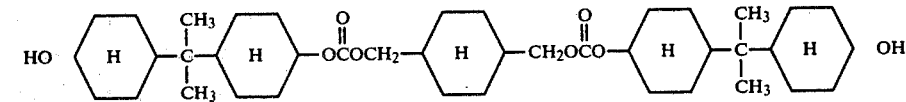

18

A = 2; G = 4,4'-isopropylidenedicyclohexylene and cyclohexane-1,
4-dimethylene; A = H; B = —G—OH

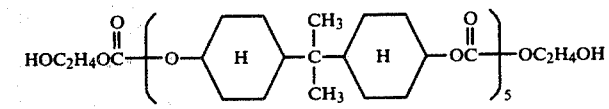

19 a = 6; G = 4,4'isopropylidenedicyclohexylene and ethylene;
A = H; B = —G—OH

TABLE 1-continued
CYCLIC DIHYDRIC ALCOHOL CARBONATE ESTERS A(―O―G―OC)$_a$―O―B
                                                                  ‖
                                                                  O

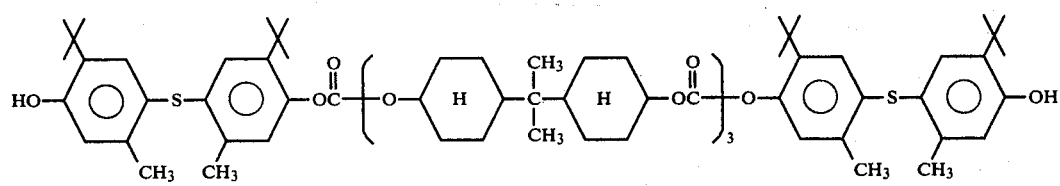

20 a = 4; G = 4,4'- isopropylidenedicyclohexylene and 4,4'-thiobis-
(2-t-butyl-5-methylphenylene); A = H; B = ―G―OH

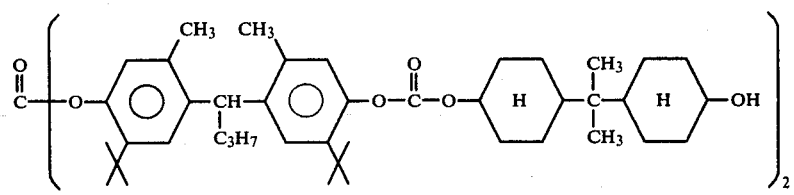

21 a = 3; G = 4,4'-isopropylidenedicyclohexylene and 4,4'-n-butyl-
5-methylphenylene); A = H; B = ―G―OH

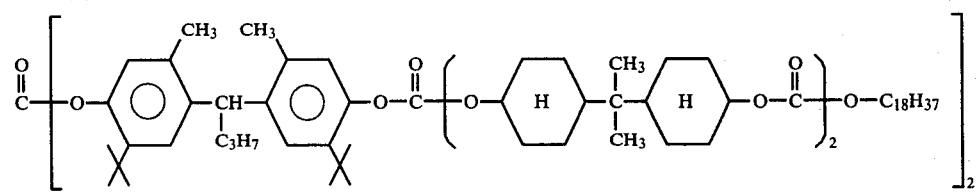

22 a = 6; G = 4,4'-isopropylidenedicyclohexylene and 4,4'-n-
butylidenebis(2-t-butyl-5-methylphenylene); A = n-octadecyloxy-
carbonyl; B = n-octadecyl

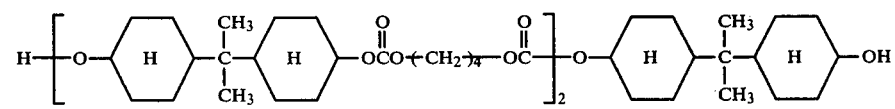

23 a = 4; G = 4,4'-isopropylidenedicyclohexylene and 1,4-tetramethylene;
A = H; B = ―G―OH

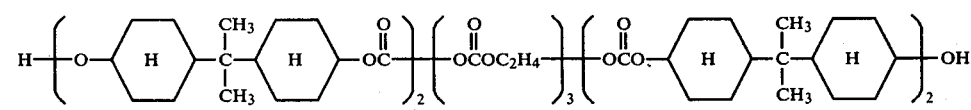

24 a = 7; G = 4,4'-isopropylidenedicyclohexylene and ethylene;
A = H; B = ―G―OH

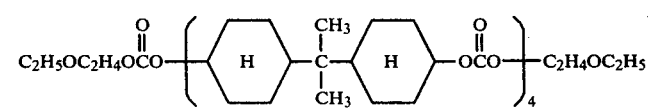

25 a = 4; G = 4,4'-isopropylidenedicyclohexylene; A = (2-ethoxy)-
ethoxycarbonyl; B = 2-ethoxyethyl

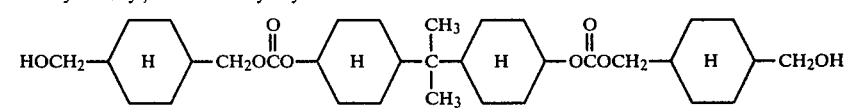

26 a = 2; G = 4,4'-isopropylidenedicyclohexylene and cyclohexane-1,4-
dimethylene; A = H; B = ―G―OH

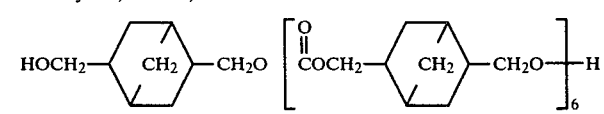

27 a = 6; G = (2,2,1)bicycloheptane-2,5-dimethylene; A = H; B = ―G―OH

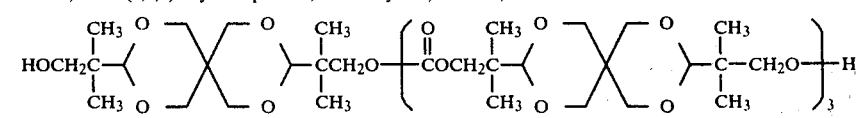

28 a = 3; G = 2,4,8,10-tetraoxaspiro(5,5)undecane-3,9-bis(1',1'-
dimethylethylene); A = H; B = ―G―OH

TABLE 1-continued

CYCLIC DIHYDRIC ALCOHOL CARBONATE ESTERS A(—O—G—OC)$_a$—O—B
‖
O

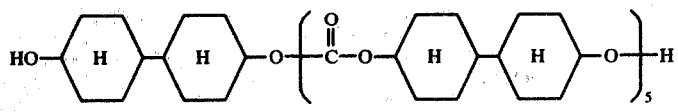

29 a = 5; G = 4,4'-bicyclohexylene; A = H; B = —G—OH

Synthesis Example—1

Synthesis of Table 1 No. 13 compound, 4,4'-isopropylidenedicyclohexyl phenyl carbonate.

Hydrogenated bisphenol A 24.0 g (0.1 mole), diphenylcarbonate 42.8 g (0.2 mole) and potassium carbonate 0.06 g were stirred at 125° C. for 3 hours under a nitrogen stream. Then the produced phenol was distilled out at 130° C. under reduced pressure. The residue was washed with methanol and white crystal of m.p. 206°–209° C. was obtained.

Synthesis Example—2

Synthesis of Table 1 No. 14 compound, 4,4',-isopropylidenedicyclohexanol carbonate tetramer.

Hydrogenated bisphenol A 9.6 g (0.04 mole), diphenylcarbonate 6.4 g (0.03 mole) and potassium carbonate 0.03 g were stirred at 130° C. for 3 hours under a nitrogen stream. Then 3.7 g of produced phenol was distilled out at 135° C. under reduced pressure. White solid material of m.p. 180°–218° C. was obtained.

EXAMPLES 1-1 to 1-10

Stabilization of a vinyl chloride polymer

| PVC | 100 parts by weight |
|---|---|
| Dioctylphthalate | 48 |
| Epoxydized soybean oil | 2 |
| Tris(nonylphenyl)phosphite | 0.2 |
| Ca-stearate | 1.0 |
| Zn stearate | 0.1 |
| Sample compound | 0.2 |

This formulation was blended and sheeted off on a two roll mill to form sheet 1 mm thick. The light resistance of these sheets was then determined by placing strips 1 cm long in a Weather-O-Meter, and exposing them to ultraviolet light. The time in hours was then noted for the sheet to develop a noticeable discoloration and/or embrittlement, indicating deterioration due to oxidation in the presence of ultra violet light (denoted as Hours to Failure in Table-2).

The following results were obtained:

TABLE - 2

| No. | SAMPLE COMPOUND | HOURS TO FAILURE |
|---|---|---|
| Control | | |
| 1-1 | None | 175 |
| 1-2 | 2-hydroxy-4-methoxybenzophenone | 330 |
| 1-3 | Diphenylcarbonate | 190 |
| EXAMPLE | | |
| 1-1 | No. 1 (Table 1) | 420 |
| 1-2 | No. 6 (Table 1) | 480 |
| 1-3 | No. 8 (Table 1) | 490 |
| 1-4 | No. 11 (Table 1) | 455 |
| 1-5 | No. 13 (Table 1) | 560 |
| 1-6 | No. 15 (Table 1) | 515 |
| 1-7 | No. 18 (Table 1) | 565 |
| 1-8 | No. 22 (Table 1) | 505 |
| 1-9 | No. 25 (Table 1) | 530 |
| 1-10 | No. 28 (Table 1) | 440 |

The results of these tests demonstrate the surprising ability of the cyclic dihydroxy compound carbonate esters of the invention to protect PVC against the harmful effects of ultraviolet light exposure. Control sample 1—1 shows that the presence of dioctyl phthalate plasticizer and epoxidized soybean oil, triaryl phosphite, and metal carboxylate additives provide minimal protection against the effects of ultraviolet without a further additive. Control sample 1-3 shows that addition of diphenyl carbonate to the base system of control 1—1 gives at most a marginal improvement, while control sample 1-2 demonstrates the pronounced effectiveness of a well-known ultraviolet stabilizer, 2-hydroxy-4-methoxybenzophenone in nearly doubling the light stability of the base formulation.

In contrast, the compositions of Examples 1—1 through 1-10 stabilized with cyclic dihydroxy compound carbonate esters of the invention, which are not in any way analogous to the known 2-hydroxybenzophenone ultraviolet stabilizer, provide dramatically enhanced light stability to well over double and in three examples more than treble the light stability of the base formulation.

EXAMPLE 2

| Polypropylene | 100 parts by weight |
|---|---|
| Stearyl beta-(4-hydroxy-3,5-di-tert-butyl-phenyl) propionate | 0.3 |
| Sample compound | 0.3 |

The composition was thoroughly blended in a Brabender Plastograph, and then compression-molded to form sheets 0.3 mm thick.

Pieces 2.5 cm$^2$ were cut off from the sheets and exposed to ultra-violet light of high-voltage mercury lamp.

And same pieces were immersed in hot water of 88° C. for 6 and 15 hours and exposed to ultraviolet light.

In each test, the time in hours required for the sheet to develop a noticeable discoloration and/or embrittlement was noted as the hours to failure.

The results obtained are shown in Table-3.

TABLE 3

| No. | SAMPLE | ORIGINAL SHEET | HOURS TO FAILURE IMMERSED 6 hrs. | 15 Hrs. |
|---|---|---|---|---|
| Control | None | 75 | 70 | 60 |
| 2-1 | Bis(2,2,6,6-tetramethyl-4-piperidinyl)sebacate | 520 | 425 | 335 |
| EXAMPLE | | | | |
| 2-1 | No. 4 (Table 1) | 565 | 480 | 425 |
| 2-2 | No. 7 (Table 1) | 590 | 545 | 485 |
| 2-3 | No. 10 (Table 1) | 610 | 550 | 505 |
| 2-4 | No. 12 (Table 1) | 640 | 595 | 550 |
| 2-5 | No. 14 (Table 1) | 655 | 620 | 575 |
| 2-6 | No. 19 (Table 1) | 625 | 575 | 525 |
| 2-7 | No. 23 (Table 1) | 610 | 565 | 520 |
| 2-8 | No. 26 (Table 1) | 635 | 595 | 560 |

The results of these tests demonstrate the surprising ability of the cyclic dihydroxy compound carbonate esters of the invention to protect polypropylene against the harmful effects of ultraviolet exposure and to retain this protecting ability even when exposed to the leaching action of hot water. Control sample 2—1 shows that polypropylene containing only a conventional phenolic stabilizer is not well protected against ultraviolet exposure. The piperidine ester stabilizer added in Control Sample 2—2 does provide good protection to the original sheet, but a significant part of this protecting ability is lost with immersion in hot water for 6 hours and even more for 15 hours.

Quite unexpectly, the cyclic dihydroxy compound carbonate esters of the invention, which are not in any way analogous to the known piperidine ester stabilizer, provide when included in the stabilizer composition used significantly better light stability to the polypropylene sheets of Examples 2—1 through 2-8 as prepared; moreover, the light stability of the hot water leached samples is dramatically better than that of Control 2—2. In all Examples, the 15 hour leached samples are as good or better than the Control 2—2 sample leached only 6 hours, and in six of the eight Examples, the 15 hour leached samples are as good or better than the Control 2—2 sample not leached at all.

EXAMPLE 3

Ethylene-vinyl acetate copolymer compositions were prepared using a stabilizer of the invention and having the following formulation:

| | |
|---|---|
| Ethylene-vinyl acetate copolymer | 100 parts by weight |
| 2,6-di-t-butyl-p-cresol | 0.1 |
| Ca-stearate | 0.1 |
| Zn-stearate | 0.1 |
| Di isodecyl phenyl phosphite | 0.2 |
| Sample compound | 0.3 |

The stabilizer was blended with the polymer on a two-roll mill at 130° C., and sheets 0.4 mm thick were then compression molded at 140° C. from the resulting blend. Pieces 2.5 cm$^2$ were cut off from the sheets and exposed to ultraviolet light in a Weather-O-Meter for 500 hours. At the start and at the conclusion of the test, the tensile strength of the sheet samples were determined.

The results are given in Table-4 as % retention of the initially determined tensile strength.

TABLE 4

| NO. | SAMPLE | % RETENTION OF TENSILE STRENGTH |
|---|---|---|
| Control | | |
| 3-1 | Phenyl salicylate | 62 |
| 3-2 | 2-Hydroxy-4-octoxybenzophenone | 67 |
| EXAMPLE | | |
| 3-1 | No. 3 (Table 1) | 81 |
| 3-2 | No. 5 (Table 1) | 83 |
| 3-3 | No. 9 (Table 1) | 85 |
| 3-4 | No. 14 (Table 1) | 88 |
| 3-5 | No. 16 (Table 1) | 86 |
| 3-6 | No. 20 (Table 1) | 85 |
| 3-7 | No. 24 (Table 1) | 84 |
| 3-8 | No. 27 (Table 1) | 83 |

The results of these tests demonstrate the surprising ability of the cyclic dihydroxy compound carbonate esters in stabilizer compositions of the invention to protect the mechanical properties of ethylene-vinyl acetate copolymer far better than known aromatic ester or 2-hydroxybenzophenone stabilizers.

EXAMPLE-4

High density polyethylene compositions were prepared using a stabilizer of the invention, and having the following formulation:

| | |
|---|---|
| High-density polyethylene | 100 parts by weight |
| Calcium stearate | 1 |
| Tetrakis(methylene-3-(3,5-di-t-butyl-4-hydroxyphenyl) propionate) methane | 0.1 |
| Distearylthiodipropionate | 0.3 |
| Sample compound | 0.3 |

The stabilizer was blended with the polymer on a two-roll mill and sheets 0.5 mm thick were prepared by compression molding of the blend. Pieces 2.5 cm$^2$ were cut off from the sheets, and exposed in a Weather-O-Meter to ultraviolet light.

The time in hours when degradation set in, as determined by a significant discoloration and/or embrittlement, was noted as hours to failure, and the results are reported in Table 5.

TABLE 5

| No. | SAMPLE | HOURS TO FAILURE |
|---|---|---|
| Control | | |
| 4-1 | 2(2'-hydroxy-5'-chlorophenyl)benzotriazole | 750 |
| 4-2 | 2,2,6,6-tetramethyl-4-piperidinyl benzoate | 560 |
| EXAMPLE | | |
| 4-1 | No. 3 (Table 1) | 1,030 |
| 4-2 | No. 6 (Table 1) | 1,150 |
| 4-3 | No. 10 (Table 1) | 1,200 |
| 4-4 | No. 12 (Table 1) | 1,310 |
| 4-5 | No. 17 (Table 1) | 1,190 |
| 4-6 | No. 21 (Table 1) | 1,250 |
| 4-7 | No. 26 (Table 1) | 1,340 |
| 4-8 | No. 29 (Table 1) | 1,070 |

The results of these tests demonstrate the surprising ability of the cyclic dihydroxy compound carbonate esters in stabilizer compositions of the invention to protect high density polyethylene against the harmful effects of ultraviolet exposure far better than known highly effective 2(2'-hydroxyaryl)benzotriazole or 2,2,6,6-tetramethylpiperidine ester stabilizers.

EXAMPLE 5

Acrylonitrile-butadiene-styrene terpolymer resin compositions were prepared using a stabilizer of the invention and having the following formulation:

| | |
|---|---|
| Acrylonitrile-butadiene-styrene terpolymer | 100 parts by weight |
| 4,4'-n-Butylidene bis-(2-t-butyl-5-methylphenol) | 0.1 |
| Sample compound | 0.3 |

The stabilizer was blended with the resin on a two-roll mill, and sheets 3 mm thick were prepared by compression molding of the resulting blend. Pieces 2.5 cm² were cut off from the sheets, and subjected to ultraviolet light in a Weather-O-Meter for 800 hours. Tensile strength before and after the test exposure was determined, and the results reported as the percent of tensile strength retained in Table-6.

TABLE 6

| No. | SAMPLE | % OF TENSILE STRENGTH RETAINED |
|---|---|---|
| Control | | |
| 5-1 | 2-(2'-hydroxy-5'-methyl-phenyl)benzotriazole | 62 |
| 5-2 | 2,4-di-t-butylphenyl-3',5'-di-t-butyl-4'-hydroxybenzoate | 49 |
| EXAMPLE | | |
| 5-1 | No. 4 (Table 1) | 81 |
| 5-2 | No. 8 (Table 1) | 88 |
| 5-3 | No. 11 (Table 1) | 87 |
| 5-4 | No. 13 (Table 1) | 90 |
| 5-5 | No. 18 (Table 1) | 89 |
| 5-6 | No. 21 (Table 1) | 86 |
| 5-7 | No. 25 (Table 1) | 84 |

The results of these tests demonstrate the unexpected ability of the cyclic dihydroxy compound carbonate esters in stabilizer compositions of the invention to protect the mechanical properties of acrylonitrile-butadiene-styrene polymer far better than known good 2(2'-hydroxyaryl)benzotriazole or aromatic ester stabilizers.

EXAMPLE 6

Polybutylene terephthalate resin compositions were prepared having the following compositions:

| | |
|---|---|
| Polybutylene terephthalate | 100 parts by weight |
| 1,3,5-tris-(3,5-di-t-butyl-4-hydroxy benzyl)-2,4,6-trimethyl benzene | 0.1 |
| Sample compound | 0.2 |

The compositions were extruded to form pellets, and then test pieces were molded from the pellets by injection molding at 270° C. Test pieces were irradiated with ultraviolet light for 500 hours in a Weather-O-Meter. Tensile strength before and after the test were determined, and the percent tensile strength retained is given in Table-7.

TABLE 7

| No. | SAMPLE | PERCENT TENSILE STRENGTH RETAINED |
|---|---|---|
| Control | | |
| 6-1 | 2,4-di-hydroxybenzophenone | 52 |
| 6-2 | bis-(2,2,6,6-tetramethyl-4-piperidinyl)sebacate | 55 |
| EXAMPLE | | |
| 6-1 | No. 2 (Table 1) | 76 |
| 6-2 | No. 7 (Table 1) | 80 |
| 6-3 | No. 9 (Table 1) | 82 |
| 6-4 | No. 14 (Table 1) | 88 |
| 6-5 | No. 15 (Table 1) | 83 |
| 6-6 | No. 19 (Table 1) | 84 |
| 6-7 | No. 24 (Table 1) | 82 |

The results of these tests demonstrate the unexpected ability of the cyclic dihydroxy compound carbonate esters in stabilizer compositions of the invention to protect the mechanical properties of polybutylene terephthalate far better than known good 2-hydroxy-benzophenone or 2,2,6,6-tetramethylpiperidine ester stabilizers.

EXAMPLE 7

Polyurethane resin compositions were prepared using stabilizers of the invention and having the following formulation:

| | |
|---|---|
| Polyurethane resin | 100 parts by weight |
| Ba-stearate | 0.7 |
| Zn-stearate | 0.3 |
| 2,6-di-t-butyl-p-cresol | 0.1 |
| Sample compound | 0.3 |

The stabilizer was blended with finely powdered polyurethane resin on a two-roll mill for five minutes at 70° C., and the sheet was then compression molded at 120° C. for five minutes to form sheets 0.5 mm thick.

Pieces 2.5 cm square were cut from the sheet, and exposed to ultraviolet light in a Weather-O-Meter for thirty hours. Elongation before and after the test was determined, and the percent elongation retained is given in Table-8.

TABLE 8

| NO | SAMPLE | PERCENT ELONGATION RETAINED |
|---|---|---|
| Control | | |
| 7-1 | methyl-alpha-cyano-beta-methyl-beta-(p-methoxyphenyl)acrylate | 49 |
| 7-2 | 2-hydroxy-4-methoxybenzophenone | 55 |
| EXAMPLE | | |
| 7-1 | No. 5 (Table 1) | 79 |
| 7-2 | No. 6 (Table 1) | 83 |
| 7-3 | No. 12 (Table 1) | 89 |
| 7-4 | No. 16 (Table 1) | 85 |
| 7-5 | No. 20 (Table 1) | 86 |
| 7-6 | No. 22 (Table 1) | 84 |
| 7-7 | No. 26 (Table 1) | 88 |

The results of these tests demonstrate the unexpected ability of the cyclic dihydroxy compound carbonate ester in stabilizer compositions of the invention to protect the mechanical properties of polyurethane resin far better than known good 2-hydroxybenzophenone or betaphenyl-alphacyanoacrylate ester stabilizers.

EXAMPLE 8

Polypropylene compositions were prepared using a stabilizer system of the invention and having the following formulation:

| | |
|---|---|
| Polypropylene | 100 parts by weight |
| 1,3,5-tris-(3,5-di-t-butyl-4-hydroxybenzyl) isocyanurate | 0.1 |
| Distearyl thiodipropionate | 0.3 |
| No. 14 compound (Table 1) | 0.2 |
| Other light stabilizers | 0.2 |

The above ingredients were thoroughly blended on a Brabender Plastograph and then compression-molded to form a sheet 0.3 mm thick. Pieces 2.5 cm$^2$ were cut off from the sheets and exposed to ultraviolet light of high-voltage mercury lamp.

The time in hours required for the sheet to develop a noticeable discoloration and/or embrittlement was noted as the hours to failure.

The results are shown in Table 9.

TABLE 9

| NO. | OTHER LIGHT STABILIZER | HOURS TO FAILURE |
|---|---|---|
| Control | | |
| 8-1 | none(without No. 14 compound) | 190 |
| 8-2 | bis(2,2,6,6-tetramethyl-4-piperidinyl) sebacate(without No 14 compound) | 420 |
| EXAMPLE | | |
| 8-1 | None | 530 |
| 8-2 | 2,2,6,6-tetramethylpiperidinylbenzoate | 930 |
| 8-3 | bis(2,2,6,6-tetramethyl-4-piperidinyl) sebacate | 1,060 |
| 8-4 | 2-hydroxy-4-methoxybenzophenone | 1,020 |
| 8-5 | 2-(2'-hydroxy-5'-methylphenyl)benzotriazole | 1,100 |
| 8-6 | 2-(2'-hydroxy-5'-chlorophenyl)benzotriazole | 1,120 |
| 8-7 | Phenyl salicylate | 850 |
| 8-8 | 2,4-di-t-butylphenyl)-3',5'-di-t-butyl-4'-hydroxybenzoate | 980 |
| 8-9 | 2,2'-thiobis(4-t-octylphenol) nickel salt | 990 |
| 8-10 | Distearyl-(3,5-di-t-butyl-4-hydroxybenzyl) phosphonate | 1,040 |
| 8-11 | Methyl-alpha-cyano-beta-methyl-beta-(p-methoxyphenyl)acrylate | 950 |

It is apparent that the stabilizer of the invention shows synergism with known ultraviolet light stablizers.

We claim:

1. A stabilizer composition capable of enhancing the resistance to deterioration of a synthetic resin when exposed to light of wavelength less than 400 nanometers, and to heat comprising a carbonate ester of a cyclic dihydroxy compound represented by the formula

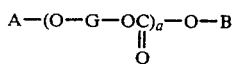

in which a is a number from 1 to 50, A is hydrogen or a group

B is a group R' or a dihydroxy compound residue —G—OH, R and R' independently of one another are alkyl, alkoxyalkyl, cycloalkyl, aryl, aryloxyalkyl, aralkyl, or alkaryl groups having 1 to 20 carbon atoms, and G independently at each occurrence is a residue of a dihydroxy compound selected from the group consisting of aliphatic dihydroxy compounds having 2 to 20 carbon atoms, bisphenols having 12 to 31 carbon atoms, and cyclic non-aromatic dihydroxy compounds having 3 to 20 carbon atoms and 0 to 4 ring oxygen atoms in 1 to 2 rings having 3 to 12 members, provided that at least one occurrence of G is a residue of a cyclic non-aromatic dihydroxy compound having 4 to 20 carbon atoms and 0 to 4 oxygen atoms disposed in 1 to 2 rings having 3 to 12 members, and 0.1 to 50 parts by weight per part by weight of carbonate ester of a polymer stabilizer selected from the group consisting of magnesium, calcium, strontium, barium, zinc and nickel salts of non-nitrogenous monocarboxylic acids having 6 to 24 carbon atoms; phenols; thiodipropionic acid esters; 1,2-epoxides; organic phosphites; 2-hydroxybenzophenones; 2(2'-hydroxyphenyl)benzo-1,2,3-triazoles; non-condensed aryl esters of non-condensed aromatic carboxylic acids; nickel phenolates and nickel ammine phenolates; alkylhydroxyphenylalkylenephosphonic acid esters and ester salts of magnesium, calcium, strontium, barium, zinc, and nickel; esters of alpha-cyanocinnamic acid and ring-substituted alpha-cyanocinnamic acids; and carboxylic acid esters of 2,2,6,6-tetraalkyl-piperidine-4-alcohols having 15 to 75 carbon atoms and 2 to 8% by weight piperidine nitrogen.

2. A stabilizer composition according to claim 1 in which in the formula of the carbonate ester A is hydrogen.

3. A stabilizer composition according to claim 1 in which in the formula of the carbonate ester B is —G—OH.

4. A stabilizer composition according to claim 1 in which in the formula of the carbonate ester G is at each occurrence a residue of a cyclic non-aromatic dihydroxy compound having 4 to 20 carbon atoms and 0 to 4 oxygen atoms disposed in 1 to 2 non-condensed rings having 3 to 12 members.

5. A stabilizer composition according to claim 1 in which in the formula of the carbonate ester G is a residue of a cycloaliphatic dihydroxy compound.

6. A stabilizer composition according to claim 1 in which in the formula of the carbonate ester G is a residue of a non-aromatic oxygen heterocyclic dihydroxy compound.

7. A stabilizer composition according to claim 1 in which the carbonate ester has a molecular weight in the range from 300 to 7000.

8. A stabilizer composition according to claim 7 in which in the formula of the carbonate ester at least one occurrence of G is a residue of an aliphatic dihydroxy compound having 2 to 20 carbon atoms.

9. A stabilizer composition according to claim 7 in which in the formula of the carbonate ester at least one occurrence of G is a residue of a bisphenol having 12 to 31 carbon atoms.

10. A stabilizer composition according to claim 8 in which the aliphatic dihydroxy compound is an alkylenediol having 2 to 6 carbon atoms in the alkylene group.

11. A stabilizer composition according to claim 9 in which the bisphenol is 4,4'-n-butylidenebis(2-t-butyl-5-methylphenol).

12. A stabilizer composition according to claim 1 in which the polymer stabilizer is calcium stearate.

13. A stabilizer composition according to claim 1 in which the polymer stabilizer is 2,6-di-t-butyl-p-cresol.

14. A stabilizer composition according to claim 1 in which the polymer stabilizer is selected from the group consisting of dilauryl thiodipropionate and distearyl thiodipropionate.

15. A stabilizer composition according to claim 1 in which the polymer stabilizer is epoxidized soybean oil.

16. A stabilizer composition according to claim 1 in which the polymer stabilizer is tri(nonylphenyl)phosphite.

17. A stabilizer composition according to claim 1 in which the polymer stabilizer is 2-hydroxy-4-n-octyloxybenzophenone.

18. A stabilizer composition according to claim 1 in which the polymer stabilizer is bis(2,2,6,6-tetramethylpiperidin-4-yl)sebacate.

19. A stabilized synthetic resin composition having enhanced resistance to deterioration when exposed to light of wavelength of less than 400 nanometers, comprising 100 parts by weight of a synthetic resin and 0.01 to 10 parts by weight of a stabilizer composition according to claim 1.

20. A stabilizer synthetic resin composition according to claim 19 in which the synthetic resin is a vinyl chloride polymer.

21. A stabilized synthetic resin composition according to claim 19 in which the synthetic resin is a polymer of an alpha-olefin having 2 to 6 carbon atoms.

22. A stabilized synthetic resin composition according to claim 19 in which the synthetic resin is an acrylonitrilebutadiene-styrene polymer.

23. A stabilized synthetic resin composition according to claim 19 in which the synthetic resin is a polyurethane.

24. A stabilized synthetic resin composition according to claim 19 in which the synthetic resin is a polymethylene terephthalate polyester.

* * * * *